United States Patent [19]

Lee

[11] Patent Number: 6,086,821
[45] Date of Patent: Jul. 11, 2000

[54] ULTRASONIC FORCE DIFFERENTIATION ASSAY

[75] Inventor: Gil U Lee, Alexandria, Va.

[73] Assignee: The United States of America as represented by the Secretary of the Navy, Washington, D.C.

[21] Appl. No.: 09/377,284

[22] Filed: Mar. 29, 1999

[51] Int. Cl.$^7$ .......................... G01N 21/00; G01N 30/96; G01N 33/543; G01N 33/553; B01D 35/06

[52] U.S. Cl. .............................. 422/20; 422/69; 422/63; 422/128; 422/99; 422/102; 422/236; 436/501; 436/518; 436/526; 436/528; 436/534; 436/536; 436/806; 436/824; 204/157.42; 204/157.62; 209/214; 210/222; 210/223; 210/695

[58] Field of Search ................................... 422/20, 69, 62, 422/128, 99, 102, 236; 436/501, 518, 526, 528, 534, 536, 806, 824; 134/1, 184; 108/20, 2, 143, 145; 204/157.42, 157.62; 209/214; 210/222, 223, 695; 366/142, 208

[56] References Cited

U.S. PATENT DOCUMENTS

| | | | |
|---|---|---|---|
| 4,467,653 | 8/1984 | Turbe | 73/620 |
| 4,484,569 | 11/1984 | Driller et al. | 128/660 |
| 4,523,122 | 6/1985 | Tone et al. | 310/334 |
| 4,571,087 | 2/1986 | Ranney | 366/108 |
| 4,575,485 | 3/1986 | Sizto et al. | 435/7 |
| 4,615,984 | 10/1986 | Stoker | 436/518 |
| 5,343,109 | 8/1994 | Mockl | 310/334 |
| 5,406,851 | 4/1995 | Li | 73/644 |
| 5,445,970 | 8/1995 | Rohr | 436/526 |
| 5,445,971 | 8/1995 | Rohr | 436/526 |
| 5,666,325 | 9/1997 | Belser et al. | 367/95 |
| 5,735,280 | 4/1998 | Sherman et al. | 128/600.03 |
| 5,770,461 | 6/1998 | Sakazume et al. | 436/526 |
| 5,779,892 | 7/1998 | Miltenyi et al. | 210/222 |
| 5,853,994 | 12/1998 | Gopinathan et al. | 435/6 |
| 5,912,182 | 6/1999 | Coakley et al. | 436/174 |
| 5,921,929 | 7/1999 | Goll et al. | 600/438 |

OTHER PUBLICATIONS

Haga et al, "Effect of Ultrasonic Irradiation on the Dissociation of Antigen–Antibody Complexes. Application to Homogeneous Enzyme Immunoassay", Chem. Pharm. Bull. 35(9) (1987), pp. 3822–2830).

Chen et al, "Ultrasound–Accelerated Immunoassay as Exemplified by Enzyme Immunoassay of Choriogonadotropin", Clinical Chemistry, 30, (1984), pp. 1446–1451.

Tarcha et al, "Absorption–enchanced Solid–Phase Immunoassay Method Via Water–Swellable Poly(acrylamide) Microparticles" Journal of Immunological Methods, 125 (1989) pp. 243–249.

Thomas et al, Measurement of Antigen Concentration by an Ultrasound–Enhanced Latex Immunoagglutination Assay, Ultrasound in Med. & Bio, vol. 22, No. 9, (1996), pp. 1277–1284.

*Primary Examiner*—Christopher L. Chin
*Assistant Examiner*—Pensee Do
*Attorney, Agent, or Firm*—Barry A. Edelberg; Ralph T. Webb

[57] ABSTRACT

An ultrasonic energy source is used to provide a variable force for measuring the binding forces between molecular entities and for sensing the presence of an analyte in a test sample. The device includes a surface that has a first binding member attached thereto and one or more particles that have a second binding member attached thereto. A reaction vessel is provided for exposing the surface to the particles whereby, if the first binding member has a binding affinity for the second binding member, a complex is formed between individual first binding members and individual second binding members and the particles thereby become immobilized with respect to the surface. The ultrasonic energy source is positioned for applying a variable ultrasonic force onto the surface, and the position of the particles is monitored as the intensity of the ultrasonic force is varied.

17 Claims, 1 Drawing Sheet

ULTRASONIC FORCE DIFFERENTIATION ASSAY

BACKGROUND OF THE INVENTION

1. Field of the Invention

The present invention relates generally to binding assays such as immunoassays and, more specifically, to the use of force generated from an ultrasonic power source to characterize specific binding interactions and to differentiate specific and nonspecific binding interactions in such assays.

2. Description of the Related Art

A remarkable ability has developed in nature for molecular recognition through the use of multiple noncovalent bonds, i.e., van der Waals, hydrogen, ionic and hydrophobic interactions, which possess a high degree of spatial and orientational specificity. Molecular recognition plays a central role in catalysis (Enzyme Structure and Mechanism, Alan Fersht, W. H. Freeman and Company, New York, 1985), cellular behavior (Bongrand, P. Physical Basis of Cell-Cell Adhesion, CRC Press: Boca Raton, Fla. 1988), the immunological response (Eisen, H. N. Immunology, $3^{rd}$ Ed., Harpers and Row Publishers: New York, 1990) and many other biological processes. The binding energy of molecular recognition interactions span at least two logs in magnitude, resulting in weak reversible interactions and interactions as strong as a covalent bond. Examples of specific molecular recognition include interactions between ligands and receptors, between enzymes and substrates, between chelators and ions, and between polynucleic acids and complementary strands. The magnitude of molecular interactions found in nature range from very weak to very strong.

Information regarding the characteristics of particular molecular interactions has enormous practical utility. For example, knowledge about the binding affinity between ligands and receptors can be used in developing screening assays to identify pharmaceutical compounds that mimic or inhibit a specific interaction. Although the structure and binding properties of molecular recognition systems can be measured, the forces involved in intermolecular interaction have remained largely unknown. Recently, it has been demonstrated that binding forces between molecular entities may be measured or characterized by conducting experiments wherein molecular entities are allowed to bond and wherein the force that is required to cause the molecular entities to separate from each other is measured. A theoretical framework for analyzing the behavior of single bonds in response to an applied force is still under development. At this time, it is clear that the binding force observed for a loading rate is determined by the binding potential of a specific molecular interaction. A theoretical framework relating these parameters is set forth in Merkell et al, "Energy Landscapes of Receptor-Ligand Bonds Explored with Dynamic Force Spectroscopy", Nature, Vol.397 (1999), pp. 50–53, in Bell, G. I., "Models for the Specific Adhesion of Cells to Cells", Science, 200, (1978), pp 618–627, and in Evans, E. et al, "Dynamic Strength of Molecular Adhesion Bonds", Biophysical Journal, 72, (1997) pp 1541–1555, all incorporated herein by reference.

Various methods have been developed for measuring binding forces. For example, micropipettes have been used in conjunction with optical microscopy to measure the interaction forces between ligands bound to model cells. In this technique one molecule is attached to a cell held in a micropipette and the other molecule is attached to another cell held in a second micropipette, allowing the two molecules to bond and then exerting a force on the cantilever that gradually increases until the molecules separate. The use of micropipettes is described by Evans, E. et al, "Dynamic Strength of Molecular Adhesion Bonds", Biophysical Journal, 72, (1997) pp 1541–1555.

Magnetically derived forces may also be used to apply force to intermolecular bonds. In this technique, one molecular entity is bound to a surface and the other molecular entity is bound to a magnetic or paramagnetic bead. Force is applied to the intermolecular bond by applying a magnetic field that pulls on the magnetic bead. As discussed below, magnetic force has been used as a way of separating bound components in immunoassays. However, the magnetic force that can be delivered to a binding site by current methods is only about 2–5 pN, which not strong enough for separating many of the binding interactions that one would typically want to study.

Binding forces between molecules can be measured by atomic force microscopy by attaching one molecule to a surface and the other molecule to an atomic force microscope cantilever, allowing the two molecules to bond and then exerting a force on the cantilever that gradually increases until the molecules separate. The use of atomic force microscopy to study intermolecular forces is described, for example, in the following patents, publications, and patent applications incorporated herein by reference: U.S. Pat. No. 5,363,697 to Nakagawa; U.S. Pat. No. 5,372,930 to Colton et al; Florin E.-L. et al, "Adhesion Forces Between Individual Ligand-Receptor Pairs" Science 264 (1994). pp 415–417; Lee, G. U et al, "Sensing Discrete Streptavidin-Biotin Interactions with Atomic Force Microscopy" Langmuir, vol. 10(2), (1994) pp 354–357; Dammer U. et al "Specific Antigen/Antibody Interactions Measured by Force Microscopy" Biophysical Journal Vol. 70 (May 1996) pp 2437–2441; Chilikoti A. et al, "The Relationship Between Ligand-Binding Thermodynamics and Protein-Ligand Interaction Forces Measured by Atomic Force Microscopy" Biophysical Journal Vol. 69 (Nov. 1995) pp 2125–2130; Allen S. et al, "Detection of Antigen-Antibody Binding Events with the Atomic Force Microscope" Biochemistry, Vol. 36, No. 24 (1997) pp7457–7463; and Moy V. T. et al, "Adhesive Forces Between Ligand and Receptor Measured by AFM" Colloids and Surfaces A: Physicochemical and Engineering Aspects 93 (1994) pp 343–348, and U.S. patent application Ser. No. 09/074,541 for "Apparatus and Method for Measuring Intermolecular Interactions by Atomic Force Microscopy", filed May 8, 1998. This method is useful for measuring intermolecular forces of individual molecules, but is slow and impractical to be used as a sensor due to the small active area that is sensed by the atomic force microscope cantilever.

Knowledge about specific binding interactions, particularly antibody-antigen interactions has led to the development of assays that exploit specific binding in determining the presence or absence of particular molecular species in test samples or in the environment. Many different types of assays are based on the specific binding of an analyte of interest (that is, whatever chemical species one is trying to detect with the assay) with one or more molecules that have a binding affinity for the analyte. In the class of techniques typically known as immunoassays, for example, detectable tags or labels are attached to antibodies that specifically bind to an analyte, and the presence of the analyte in a test sample is detected by detecting the formation of labeled antibody-analyte complexes or by measuring the amount of labeled antibody that remains unbound. Other types of binding molecules such as chelators, strands of polynucleic acids and receptors may also be used in binding assays.

In a conventional solid phase assay, molecules that have a binding affinity for an analyte are immobilized onto a solid surface, and the surface is exposed to a test sample. The analyte, if present in the test sample, binds to the immobilized binding member. Various methods have been used to generate a macroscopically observable signal to indicate that such binding has occurred. For example, a labeled reagent that binds to the analyte or that binds to the binding member-analyte complex (as in, for example, a sandwich assay) may be added to the test sample. Various types of labels including radioactive, enzymatic, fluorescent and infrared-active have been used for creating labeled reagents.

Magnetically-active beads have been used as labels in immunoassays. See, for example, the following U.S. patents and patent applications, incorporated herein by reference: U.S. Pat. No. 5,445,970 to Rohr and U.S. Pat. No. 5,445,971 to Rohr, and U.S. Pat. application Ser. No. 09/008,782 for "Force Discrimination Assay" by Gil U Lee, filed on Jan. 20, 1998.

In binding assays of all types, including those that use magnetically-active beads, a persistent problem is the occurrence of false positive results. False positives may be caused by nonspecific binding of labeled reagents to the surface, by cross-reactivity of a labeled reagent with compounds that are analogs of the analyte or by gravitational settling of a labeled reagent onto the surface of the surface. Each of these events can cause an excess of labeled reagent to remain on an assay surface. False positives results may be reduced by applying a force to a surface that is sufficient to remove undesirable or excess labeled reagent but that is not sufficient to disrupt the specific binding that is being measured in the assay. Methods of force differentiation previously described include centrifugation, hydrodynamics and magnetic force transduction. For example, in an assay using magnetically-active beads, magnetic force may be applied to remove beads that settle onto the surface due to gravitational force. However, magnetic force alone is often insufficient to dislodge beads that bind to the surface by nonspecific binding or by cross-reactivity with an analog of the analyte. As described in U.S. pat. application Ser. No. 09/008,782, nonspecific binding of labeled reagents to a surface can be reduced by chemically modifying the surface to reduce nonspecific adhesive forces.

Centrifugation may be used to apply force to rupture bonds between molecular entities. A disadvantage of centrifugation is that it is difficult to make an accurate calculation of the amount of force that is delivered to a binding site. Centrifugal force must be applied over an extended period of time (during acceleration and deceleration) and the force has components of torque caused by the acceleration and deceleration.

Hydrodynamic forces may also be used to apply force to rupture bonds between molecular entities. A use of hydrodynamic force to study receptor-mediated adhesion is described in Cozen-Roberts et al, "Receptor-Mediated Adhesion Phenomena" Biophys. J. 58 (1990), pp 107–125, incorporated herein by reference. This technique has the disadvantages that it produces off-axis forces and requires a complex flow cell arrangement.

Ultrasonic force has used commercially for a wide variety of industrial and medical purposes including imaging, welding, cleaning, and dispersing solids in a liquid medium. In the field of solid phase assays, the use of ultrasonic force has, up until now, been limited to enhancing the reactivity of a solid phase binder (see, for example, Chen et al, "Ultrasound-Accelerated Immunoassay as Exemplified by Enzyme Immunoassay of Choriogonadotropin", Clinical Chemistry, 30, (1984), pp 1446–1451 or Tarcha et al, "Absorption-enhanced Solid-Phase Immunoassay Method Via Water-Swellable Poly(acrylamide) Microparticles" Journal of Immunological Methods, 125 (1989) pp 243–249 or dissociating binder-ligand complexes so that the amount of ligand can be measured or so that the binder can be reused (see, for example, U.S. Pat. No. 4,615,984 to Stoker, incorporated herein by reference, and Haga et al, "Effect of Ultrasonic Irradiation on the Dissociation of Antigen-Antibody Complexes. Application to Homogeneous Enzyme Immunoassay", Chem. Pharm. Bull. 35(9) (1987), pp 3822–2830).

SUMMARY OF THE INVENTION

Thus, it is an object of the present invention to provide a method of characterizing binding forces between binding members wherein the force that is applied can be varied and is strong enough to separate intermolecular complexes.

Further, it is a object of the present invention to provide a method of characterizing binding forces between binding members wherein the force that is applied is oriented primarily in the direction of the molecular interaction and wherein off-axis or tangential forces are minimized.

Further, it is a object of the present invention to provide a method for characterizing binding forces between binding members that does not require complex and expensive apparatus.

Further, it is an object of the present invention to provide a method for characterizing binding forces between binding members that can test a large number of binding members simultaneously and quickly.

It has now been discovered that force generated from an ultrasonic power source can be used in an assay to measure or characterize molecular interactions, such as binding affinities of ligands and receptors. This is done by attaching a binding member to a bead or other particle that can be observed in real time, for example, through a microscope, and then allowing the particle-bound binding member to bind with a surface-bound binding member to form a complex. The presence of complexes on the surface is detected by observing the presence of immobilized particles on the surface. Ultrasonic force is then applied, and the movement or lack of movement of the particles, indicating dissociation or lack of dissociation of the complexes may be observed by microscopy or other methods of detection. Alternatively, the ultrasonic force may be applied at a strength level that is insufficient to separate binding members from each other (while dislodging particles bound to the surface by nonspecific interactions) and then gradually increased to the point where the surface-bound binding member and the particle-bound binding member separate and the particles become mobile on the surface. By this same method, the binding strength of different compounds can be measured and compared simultaneously by providing a surface having the different binding members attached to spatially distinguishable areas and by observing on which areas of the surface the particles remain bound as the strength of the ultrasonic force is increased. It is also possible to measure the binding strength of different compounds simultaneously by attaching each different compound to a different distinguishable class of particle and then observing which classes of particles remain bound as the strength of the ultrasonic force is increased.

Therefore, in one aspect, a device and method are provided to measure the binding forces of a first binding member with a second binding member. In this embodiment, a surface is provided that has a first binding member attached thereto, and one or more particles are provided that have a second binding member attached thereto. A reaction vessel is provided for exposing the surface to the particles whereby, if the first binding member has a binding affinity for the second binding member, a complex is formed between individual first binding members and individual second binding members and the particles thereby become immobilized with respect to the surface. An ultrasonic force means is operatively disposed with respect to the surface for applying a variable ultrasonic force onto the surface and a means is provided for monitoring the position of the particles with respect to the surface, particularly as the intensity of the ultrasonic force is varied, so that the intensity level at which the complex breaks can be noted. In an alternative embodiment, the surface can include spatially addressable subregions, with each subregion having a different surface-bound binding member attached thereto. This embodiment of the device can be used to measure the binding forces of a plurality of different surface-bound binding members. In another alternative embodiment, the binding forces of a plurality of different particle-bound binding members may be measured by attaching each type of binding member to a different distinguishable class of particle.

It is also an object of the present invention to provide a binding assay (that is, an assay using binding interactions to determine the presence or absence of an analyte) wherein false positive results are minimized by removing labeled molecular entities that are not bound by specific binding interactions.

It has also been discovered that ultrasonic force can be used in a binding assay to dislodge and remove labeled compounds that adhere nonspecifically to a surface or that become bound due to cross-reactivity with an analog of an analyte. By the dislodging and removal of labeled compounds that are not bound by specific binding reactions, false positive results can be greatly reduced and the sensitivity of a binding assay can be improved.

Therefore, according to another aspect, the present invention is an assay device and method for detecting the presence or amount of an analyte in a test sample. In this embodiment, a surface is provided that has immobilized binding members that bind specifically to an analyte attached thereto, a reaction vessel for exposing the surface to the test sample, and a labeled reagent that, when contained in the test sample and exposed to the surface, becomes immobilized with respect to the surface specifically in relation to the amount of the analyte in the test sample. An ultrasonic force means is operatively disposed with respect to the surface for applying an ultrasonic force onto the surface for dislodging any of the labeled reagent that binds non-specifically to the surface or that becomes immobilized on the surface of the surface due to cross-reactivity with an analog of the analyte, and a means is provided for detecting the amount of labeled reagent that remains immobilized with respect to the surface after the ultrasonic force is applied. In one embodiment, the labeled reagent of the assay device is in the form of a plurality of particles that have second binding members attached thereto, wherein the second binding members are capable of undergoing a selective binding interaction in relation to the amount of the analyte in the test sample, and the assay device includes a means to observe the particles during and after the application of the ultrasonic force. In an alternative embodiment, the surface can include spatially addressable subregions, with each subregion having a different surface-bound binding member attached thereto so that a plurality of analytes can be detected simultaneously in one assay.

It has also been discovered that ultrasonic force may be used in a "two-bead" assay, (that is, an assay using binding interactions between two or more types of particles to determine the presence or absence of an analyte). In this embodiment, ultrasonic force is used to dislodge particles that bind to each other by nonspecific binding.

DETAILED DESCRIPTION OF THE PREFERRED EMBODIMENTS

Definitions

Figure 1:
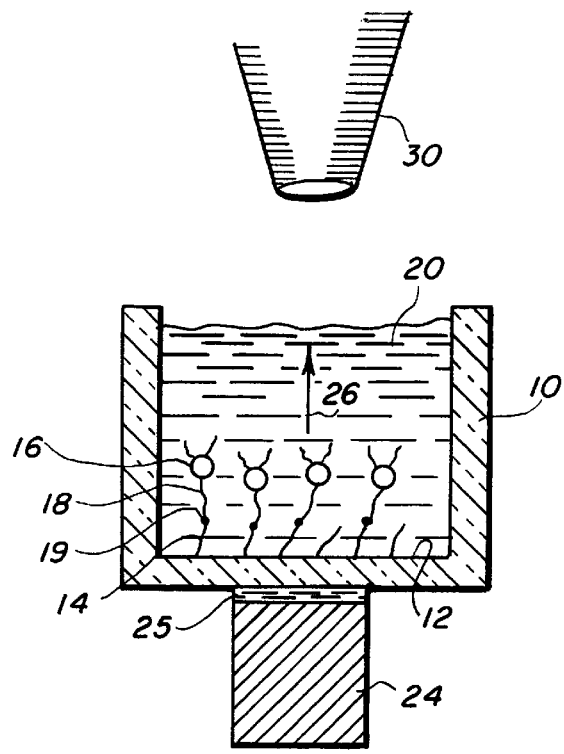
FIG. 1 is a schematic view of an assay device of the present invention having a transmission of ultrasound through an assay cell wall.

As used herein, the term "binding member" refers to a member of a binding pair, that is, two different molecules wherein one of the molecules specifically binds to the second molecule through chemical or physical means. In addition to the well-known antigen and antibody binding pair members, other binding pairs include, but are not intended to be limited to, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), sugar and boronic acid, and similar molecules having an affinity which permits their association in a binding assay. A binding member may also be made by recombinant techniques or molecular engineering. If the binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other binding members. The details of the preparation of such antibodies, peptides and nucleotides and their suitability for use as binding members in a binding assay are well-known to those skilled-in-the-art. A binding member may also be part of a cell, virus or other biological entity that is immobilized on a surface or on a particle. The term "binding member" also refers to a member of any pair of compounds wherein the binding affinity between them is unknown or is the subject of experiments under the method of the present invention.

As used herein, the term "first binding member" refers to a binding member that is attached to the surface and the term "second binding member" refers to a binding member that is attached to a particle. These are also referred to as the "surface-bound" binding member and the "particle-bound" binding member respectively.

The term "binding member" as used herein, usually refers collectively to a plurality of molecules of the same chemical identity (in much the same way that the term "compound" generally refers collectively to a plurality of identical molecules). In descriptions relating to the formations of complexes, it is sometimes necessary to describe the interaction of single molecules of the surface-bound and particle-bound binding members. In these instances, the term "individual" binding members is used. The term "different" binding members refers to binding members having a different chemical identity.

The term "surface", as used herein, refers to any solid material that has first binding members attached to it. Preferably, the surface makes up the bottom or sides of a reaction vessel. Most preferably, the surface is a flat portion of the bottom of a reaction vessel and has an area that is approximately coequal with the field of view of an optical microscope positioned above the reaction vessel. An example of a suitable surface for the present invention is an region of about 100×100 microns on the bottom of a microtitre well.

The term "particle", as used herein, refers to any mobile material that has a surface area that has binding members attached to it. The particles should be large enough so that binding members can be easily attached and so that the position of the particles can be easily monitored, yet they should be small enough so that the particles and their attached binding members can easily participate in binding reactions with the binding members immobilized on the surface. Preferably, the particles should be large enough to be visible through a light microscope. Preferably, the particles have an average diameter of between about 5 nm and about 1 mm and, more preferably, have a diameter between about 0.2 $\mu$m and about 200 $\mu$m. Preferably, the particles are magnetic, paramagnetic or non-magnetic spherical beads.

The requirement that the surface a nd the particles have binding members attached to them is met by any covalent or non-covalent form of attachment of the binding members to the surface and the particles, either directly or through any type of linking group. The binding members should be bound to the surface and to the particles strongly enough so they are not displaced by the application on the ultrasonic force during the practice of the method of the present invention.

The term "complex" refers to any intermolecular entity formed by a binding interaction between a surface-bound binding member and a particle-bound binding member that causes the particle to become immobilized with respect to the surface due to the force of the binding interaction.

The term "reaction vessel" refers to any type of receptacle or holder that provides a way for the surface to be exposed to the particles. Typically, the surface will be submersed in a liquid medium and will be exposed to particles suspended in the liquid medium. The reaction vessel, therefore, is preferably of a shape that allow it to retain a liquid medium. For example, a typical microliter well or assay cell can be used as the reaction vessel. In one device configuration, ultrasound is transduced through one or more of the reaction vessel walls. In this case, the thickness of the walls, their material of construction and geometry must be optimized to transmit sound. In a second device configuration, ultrasound is generated in the solution of the reaction vessel, and in this case the reaction vessel must be constructed to reflect sound. The general principles of vessel design are outlined below.

The term "ultrasonic force" refers to any acceleration force applied by means of a longitudinal or transverse pressure wave arising from an ultrasonic source, such as an ultrasonic transducer. The terms "ultrasonic force means", "ultrasonic power source" and "ultrasonic sound source" all refer interchangeably to any apparatus, such as an ultrasonic transducer, that is capable of imparting an ultrasonic force. Preferably, the ultrasonic force means is an ultrasonic piezo electromechanical transducer. The term "variable force" refers to an ultrasonic force that can be controlled and varied, particularly across a range of intensities from a force that is too weak to separate binding member complexes to a force that is strong enough to separate binding member complexes. Preferably, the amplitude, frequency, pulse rate, pulse duration, and wave-form of the ultrasonic force are all selectable and controllable so that the force delivered to the binding member complexes can be fine-tuned and ramped. In a typical ultrasonic piezo transducer, these variables can be controlled by controlling the voltage input to the transducer through an external function generator and power amplifier.

The terms "operatively disposed" or "operatively coupled", when used herein to describe the relationship between the surface and the ultrasonic force means, refers to any method of coupling a source of ultrasonic force to the reaction vessel or to a medium contained in a reaction vessel so that ultrasonic force is delivered to the surface and the particles.

The phrase "means for monitoring the position of the particles with respect to the surface", as used herein, refers to any means of determining whether particles are immobilized on the surface, thereby indicating whether there is sufficient binding affinity between surface-bound binding members and particle-bound binding members to form complexes, and whether any immobilized particles are moved off of or around the surface by the application of the ultrasonic force, thereby indicating whether the applied force was strong enough to separate the complexes. Preferably, the monitoring is done by optical microscopy. This can be achieved by simply positioning a microscope so that the surface and any particles immobilized thereon can be observed. Preferably, the position-monitoring is automated by providing, for example, a digital image acquisition system and processing system for recording digital images of the surface and for identifying and counting particles that are immobilized thereon. Other possible means of monitoring the presence and position of particles on the surface include, for example, fluorescent detection, color detection, electrochemical detection, magnetic detection, measurement of weight differences, and chemical detection, such as detection of enzymatic reactions.

As used herein, the phrase "characterizing the binding forces" between binding members refers to any assay or experiment that results in the gaining of knowledge about interactions between particle-bound binding members and surface-bound binding members that can be achieved by means of the device and methods described herein. It may be possible to use the device and methods of the invention to calculate the magnitude of binding forces between binding members. Additionally, the device and methods of the invention may be used to calculate relative binding forces of different binding members, either by conducting successive experiments with different binding members or by conducting simultaneous experiments using the alternative embodiments of the invention. For example, to measure the binding forces of a plurality of different surface-bound binding members simultaneously, a device is provided in one embodiment of the invention wherein the surface includes a plurality of subregions that each have a different spatially distinguishable subregions that each have a different surface-bound binding member attached thereto. What is meant by the term "spatially distinguishable subregions" is that if, during an experiment, a particle binds to a particular part of the surface, there is some way to determine, by the particle's spatial location on the surface, the identity of the surface-bound binding member to which the particle has attached. Any method of creating patterned surface, such as, for example photo-patterning or contact printing methods may be used to create spatially distinguishable subregions. As another example, to measure the binding forces of a plurality of different particle-bound binding members simultaneously, a device is provided in another embodiment of the invention wherein a plurality of particles of different distinguishable classes are provided that have a different particle-bound binding member attached to each class of particle. If, during an experiment, a particle binds to the surface, the identity of the particle-bound binding member can be determined according to the class of the particle. Any classification system for particles may be used that allows classes of particles to be distinguished from each other. For example, particles may be classified by size, density, fluorescent properties, magnetic properties, or color. When optical microscopy is the means used for detecting particles, a system of classification of particles based on size is preferred.

The term "test sample", as used herein, refers to a material suspected of containing the analyte. The test sample can be used directly as obtained from the source or following a pre-treatment to modify the character of the sample. The test sample can be derived from any biological source, such as a physiological fluid including, but not intended to be limited to blood, saliva, ocular lens fluid, cerebral spinal fluid, sweat, urine, milk, ascites fluid, mucous, synovial fluid, peritoneal fluid, amniotic fluid and the like; fermentation broths; cell cultures; chemical reaction mixtures and the like. The test sample can be pre-treated prior to use, such as preparing plasma from blood, diluting viscous fluids, and the like. Methods of treatment can involve filtration, distillation, concentration, inactivation of interfering components, and the addition of reagents. In addition to biological or physiological fluids, other liquid samples can be used such as water, food products and the like for the performance of environmental or food production assays. In addition, a solid material suspected of containing the analyte can be used as the test sample. In some instances, it may be beneficial to modify a solid test sample to form a liquid medium or to release the analyte.

The term "analyte" or "analyte of interest", as used herein, refers to the compound or composition to be detected or measured and which has at least one epitope or binding site. The analyte can be any substance for which there exists a naturally occurring binding member or for which a binding member can be prepared. Analytes include, but are not intended to be limited to, toxins, organic compounds, proteins, peptides, microorganisms, amino acids, carbohydrates, nucleic acids, hormones, steroids, vitamins, drugs (including those administered for therapeutic purposes as well as those administered for illicit purposes), virus particles and metabolites of or antibodies to any of the above substances. For example, such analytes include, but are not intended to be limited to, ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide; antibodies to rubella, such as rubella-lgG and rubella-lgM; antibodies to toxoplasmosis, such as toxoplasmosis IgG (Toxo-lgG) and toxoplasmosis IgM (Toxo-lgM); testosterone; salicylates; acetaminophen; hepatitis B virus surface antigen (HBsAg); antibodies to hepatitis B core antigen, such as anti hepatitis B core antigen IgG and IgM (Anti-HBC); human immune deficiency virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP); and drugs of abuse and controlled substances, including but not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methaqualone; opiates such as heroin, morphine, codeine, hydromorphone, hydrocodone, methadone, oxycodone, oxymorphone and opium; phencyclidine; and propoxyhene. The term "analyte" also includes any antigenic substances, haptens, antibodies, macromolecules and combinations thereof.

The term "analog of the analyte", as used herein, refers to a substance which cross-reacts with an analyte-specific binding member, though to a lesser extent than does the analyte itself. Such an analog, as defined in this application, is a substance whose presence in a test sample can lead to false positive results if the analog is not removed from the assay.

The term "labeled reagent", as used herein, refers to a substance that has a detectable label and that becomes immobilized with respect to the surface in relation to the amount of analyte in a test sample. Typically, the labeled reagent will be a compound that has some type of label attached to a binding member that binds directly or indirectly to the analyte. Preferably the label is a magnetic or nonmagnetic bead, but other types of labels such as radioactive or enzymatic labels may be used. (In this aspect of the invention, it is not necessary that the labeled reagent be a particle) The attachment of the label to the binding member may be affected by covalent or non-covalent binding means, linking arms, and the like. However, the method of attachment is not critical to the present invention. The label allows the reagent to produce a detectable response that will be directly or indirectly related to the amount of analyte in the test sample.

In this embodiment of the invention, it is not necessary that the labeled reagent be a particle, as defined above, or that the labeled reagent bind directly to the surface. All that is necessary is that the assay involves some type of binding event that causes the labeled reagent to become immobilized with respect to the surface in some detectable or identifiable manner, that this immobilization can be correlated either directly or indirectly with the amount of analyte in the test sample and that there is a potential for false positive results in the assay due to binding events that are not correlated with the amount of analyte in the test sample. According to this aspect of the invention, ultrasonic force is used to separate and remove non-specifically bound labeled reagent.

In a binding assay according to the present invention, excess analyte or nonspecifically bound particles that are dislodged by the application of ultrasonic force are removed from the assay surface. To accomplish this, the ultrasonic force may be used in conjunction with additional forces such as, for example, magnetic force, optical force, electrostatic force, hydrodynamic force, gravitational force or combinations thereof.

Description of Devices

Figure 2:
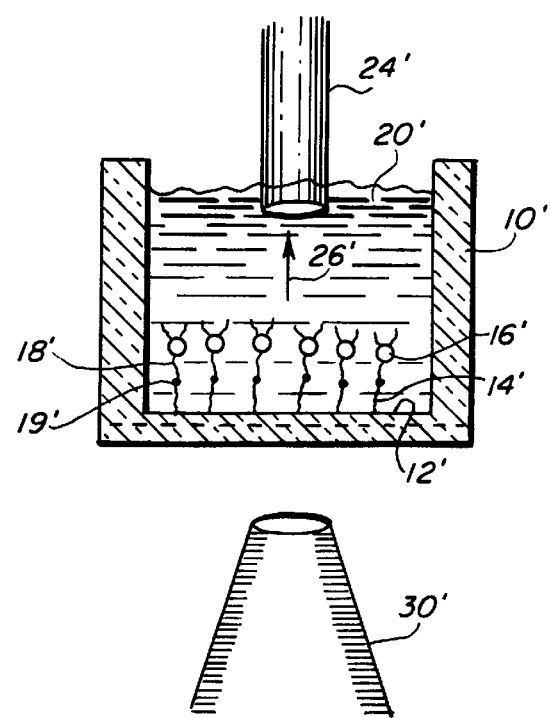
FIG. 2 is a schematic view of an assay device of the present invention having an ultrasound source immersed directly in an liquid medium of an assay cell.

The devices of the present invention are illustrated schematically in FIGS. 1 and 2, which depict two alternative preferred means by which an ultrasonic transducer may be operatively disposed with respect to the surface for applying a variable force on the particles. Of course, the present invention is not limited to these two alternatives, and any means for coupling an ultrasonic source to apply an ultrasonic force to the surface may be used.

In FIG. 1, a reaction vessel 10 includes a bottom surface 12 having surface-bound binding members 14. The reaction vessel 10 includes a liquid medium 20. A plurality of particles 16 have particle-bound binding members 18 that have an affinity for the surface-bound binding members, so that complexes 19 are formed between the surface-bound binding members and the particle-bound binding members. An ultrasonic sound source 24 is positioned so that ultrasound is transmitted through a conduction medium 25, such as water, and through the bottom surface of the assay cell to impart a force (represented by arrow 26) onto the particles. A microscope 30 is positioned so that movement of the particles can be monitored.

In FIG. 2, a reaction vessel 10' includes a bottom surface 12' having surface-bound binding members 14'. In this embodiment, the bottom surface 12' is made of a transparent material. The reaction vessel 10' includes a liquid medium 20'. A plurality of particles 16' have particle-bound binding members 18' that have an affinity for the surface-bound binding members, so that complexes 19' are formed between the surface-bound binding members and the particle-bound binding members. An ultrasonic sound source 24' is positioned so that it is submersed in the liquid medium of the reaction vessel so that ultrasound is transmitted into the liquid medium of the reaction vessel to impart a force (represented by arrow 14') onto the particles. A microscope 30' is positioned so that movement of the particles can be monitored through the transparent bottom surface 12'.

As explained below, it is easiest to understand how the force is applied to the beads in the force configuration depicted in FIG. 1. However, the efficiency in transmitting an ultrasonic force to the particles is severely attenuated by the reaction vessel wall in the first configuration and thus the configuration in FIG. 2 is preferred.

In its simplest form, the device of the present invention allows for the investigation of binding forces between a surface-bound binding member and a particle-bound binding member. Alternative embodiments of the devices of the invention allow for the screening of multiple surface bound binding members or multiple particle-bound binding members in a single experiment and for detecting multiple analytes. For example, to screen a plurality of different surface-bound binding members at the same time, the surface can be subdivided into a plurality of different subregions and a different surface-bound binding members can be attached to each subregion. The different binding members can be attached to the different subregions by any method for creating patterned substrates, such as photo-patterning or contact printing. The subregions should be positioned with respect to each other so that they are spatially distinguishable, preferably so that they can be distinguished from each other by optical microscopy. As another example, to screen a plurality of different particle-bound binding members at the same time, the different binding members can be attached to different, distinguishable classes of particles.

Description of Methods

Either the configuration of FIG. 1 or the configuration of FIG. 2 may be used in the methods of the present invention. The procedure for using a device of the present invention to characterize binding forces is to contact the particles with the surface so that if the particle-bound binding members have a binding affinity for the surface-bound binding members, complexes are formed and particles become immobilized on the surface. Preferably, the surface and the particles are submerged in a liquid medium during the steps of this process. The presence of the particles immobilized on the surface may be monitored by, for example, observing them by optical microscopy. An ultrasonic force is then applied to the particles and any resulting change in the position of the particles and, in particular, in the number of particles that remain immobilized on the surface, is noted. Preferably, the ultrasonic force is applied at an intensity that is too weak to have any effect on any of the particles and is increased gradually or in stages until it is sufficient to completely rupture all complexes and cause all the particles to become mobile. The number of immobilized particles can be counted at each stage and plotted as a function of the amount of force that is applied. Alternatively, a force of a given intensity can be applied and held and the behavior of particles as a function of time in response to the applied force can be observed and recorded.

The ultrasonic force can be applied in conjunction with other forces such as magnetic force, optical force, hydrodynamic force, gravitational force and combinations thereof. These additional forces are helpful in applying force to a particle over a wide range of time and removing dislodged particles from the field of view of the experiment.

The procedure can be repeated to generate sets of data regarding particular ligands and receptors. The procedure for simultaneously characterizing the binding forces of a plurality of surface-bound binding members with a particle-bound binding member is essentially the same, except that in the step of monitoring or observing the particles that are immobilized on the surface, the spatial location of the particles is noted, so that is can be determined which subregions have particles attached to them and which subregions do not have particles attached to them at any given level or ultrasonic force. In this way, the relative binding strength of different surface-bound binding members can be determined.

The procedure for simultaneously characterizing the binding forces of a surface-bound binding member with a plurality of different particle-bound binding members is essentially the same, except that in the step of monitoring or observing the particles that are immobilized on the surface, the classification of the particles (for example, the size of the particle) is noted, so that is can be determined which class of particle remains attached to the surface and which class of particle does not remain attached to the surface at any given level or ultrasonic force. In this way, the relative binding strength of different particles-bound binding members can be determined.

The present invention also includes methods of conducting assays to determine the presence of an analyte in a test sample. Again, either the configuration of FIG. 1 or FIG. 2 may be used. In assays to determine the presence of an analyte, the ultrasonic force that is applied is selected so that it is sufficiently strong to dislodge any of the labeled reagent or particles that bind non-specifically to the surface or that becomes immobilized on the surface due to cross-reactivity with an analog of the analyte and is not strong enough to dislodge labeled reagent or particles that are immobilized on the surface due to specific binding. In other words, ultrasonic force is used to decrease the background from an assay and thereby increase the accuracy of the assay. The appropriate amount of ultrasonic force to be is applied will vary according to the particulars of a given assay and can be readily determined by conducting a few test runs before an assay is used in practice for diagnostic purposes or for environmental sensing. The ultrasonic force can be applied in conjunction with other forces such as magnetic force, optical force, hydrodynamic force, gravitational force and combinations thereof to remove dislodged labeled reagent or particles from the assay device. The assay device and methods can be readily modified for conducting simultaneous assays for the identification of multiple analytes in a single assay by providing patterned surfaces and different binding members on different classes of beads.

The present invention also includes a device and method for conducting a "two-bead" assay, that is an assay wherein the relevant binding event is between two different types of particles. In the devices and methods of this embodiment, instead of providing means to monitor beads on a surface, means are provided for monitoring the presence of bead complexes.

Considerations for Selecting or Modifying the Ultrasonic Force

The following discussion relates to considerations to be taken in to account in modifying an ultrasonic sound source for use in the present invention.

The exact force that can be exerted on a binding complex depends on several controllable variables, including the intensity and character of the ultrasound source, the shape, size and composition of the cell or vessel in which the assay is performed and the type of interface between the ultrasound source and the cell.

A sound wave is a longitudinal wave that is described by the equation $$x = x_o \sin(2\pi f t),$$

where x is the displacement of the molecules in the medium, $x_o$ is the displacement amplitude and $f$ is the frequency of the wave. It follows that the velocity (v) and acceleration ($\alpha$) of this wave are $v = v_o \sin(2\pi f t)$ and $\alpha = \alpha_o \sin(2\pi f t)$, respectively, where $v_o = 2\pi f x_o$ and $\alpha_o = (2\pi f)^2 x_o$. The power of a sound wave is described by its intensity (W/cm²)

$$I = P_A^2 / 2\rho c,$$

where $P_A$ is the pressure amplitude ($P_A = v_o \rho c$), $\rho$ is the density of the medium of the wave and c is the speed of sound in the medium.

Typical commercial power ultrasonic transducers operate at 20 kHz with an intensity of 1 W/cm² of power. The acceleration amplitude ($\alpha_o$) of the sound waves generated by such transducers is 15,800 M/s². Either increasing the frequency of the transducer to 40 kHz or the intensity to 4 W/Cm² will produce 1,000 pN forces, which is significantly larger than the forces that have been measured between some of the strongest ligand-receptor pairs.

Typical commercial 20 kHz ultrasound transducers used for cleaning purposes are optimized to produce vigorous cavitation and heating and thus should be modified to be useful in the methods of the present invention. In the methods of the present invention, cavitation and heating are undesirable because the forces of cavitation and effects of heating could destroy or rupture any binding complexes indiscriminately and could cause binding members to become detached from the surface and from the particles. Cavitation in a medium exposed to ultrasound is caused by the formation of gas bubbles. Cavitation can be avoided by increasing the frequency of the ultrasound or by using pulsed sound waves. At frequencies beyond 20 kHz, cavitation decreases because gas bubbles do not have time to form. To minimize cavitation and to provide a more controllable force for force differentiation purposes, frequencies in the range of 80 kHz–10 MHz are optimal. Cavitation can also be avoided by using pulsed sound waves. It has been found that when ultrasound is introduced into a medium, there is a delay between the introduction of sonic energy and the onset of cavitation. For example, a 20 kHz wave requires a pulse of at least 20 msec to produce cavitation. Therefore, cavitation can be avoided by using pulsed waves with pulses of less than 20 msec.

Another modification that can be made to conventional ultrasound generating systems to improve their usefulness in the methods of the present invention is to alter the waveform to a triangle or sawtooth waveform. Typical conventional ultrasound generating systems produce a sine or square waveform. In the methods of the present invention, these wave-forms will cause the particles to move towards and away from the surface at equal forces. Acceleration of particles toward the surface is undesirable because it will lead to increased loading forces, increased areas of contact and increased adhesion. A saw tooth or triangular waveform that is designed to rapidly accelerate the particles away from the surface and slowly accelerate the particles towards the surface is preferable.

Another consideration to be taken into account in designing a device according to the present invention is the manner in which the ultrasonic force is transmitted to the surface. As described above, an ultrasonic force generator may be positioned so that ultrasonic force is transmitted through the bottom of the reaction vessel (FIG. 1) or it may be immersed in a liquid medium in the reaction vessel so that the ultrasonic force is transmitted directly through the liquid medium to the surface. The efficiency of the transmission of a longitudinal pressure wave from one medium into another is determined by the acoustic impedance (R) of the medium which is equal to the product of the density and speed of sound in the medium. The acoustic impedance of several materials are presented in Table 1.

TABLE 1

| Acoustic Impedance of Materials | |
| --- | --- |
| Material | R (g/cm2sec) |
| Steel | 475 |
| Quartz | 144 |
| Plexiglass | 32 |
| Water | 15 |
| Air | 0.043 |

For planar surfaces, the reflection pressure ratio (Pr/Pi), transmission pressure ratio (Pt/Pi), sound power reflection coefficient (r) and sound power transmission coefficient (t), from medium 1 into 2 are, $$Pr/Pi = (R2 - R1)/(R2 + R1)$$

$$Pt/Pi = 2R2/(R2 + R1)$$

$$r = [(R2 - R1)/(R2 + R1)]2$$

$$t = 4R2R1/(R2 + R1)2$$

Note that the pressure can actually increase as the sound passes from one phase to another while the intensity actually decreases and that a longitudinal wave is transduced more efficiently from a low-to-high impedance material than from a high-to-low impedance material. This means that the highest sound intensities will be produced when a metal ultrasonic horn is immersed in the liquid of the cell (FIG. 2). However, by choosing materials carefully and including a liquid conduction medium the transmission of ultrasonic power across two solid interfaces can be achieved will as little as 50% attenuation. The fact that sound can be transmitted across solid surfaces suggests that the configuration shown is FIG. 1 may be used, but two additional consideration must be taken into account. First, the intensity of sound in a solid decays exponentially into a solid, and the decay factor is inversely related to the square of the frequency of sound. The decay of sound suggests that the walls of the cell should be made as thin as possible to avoid undesirable levels of attenuation. Second, solids can support transverse waves and these waves manifest themselves at liquid-solid interfaces. Transverse acoustic waves take on at least three different forms: surface acoustic waves, Lambs waves and Love waves. These transverse waves produce lateral displacement and acceleration at the surface which can produce torque on the beads and amplifies the force delivered to the ligand-receptor interaction. The result is that secondary lateral effects can have strong effects and can lead to inhomogeneous force transduction across a surface.

Having described the invention, the following examples are given to illustrate specific applications of the invention, including the best mode now known to perform the invention. These specific examples are not intended to limit the scope of the invention described in this application.

EXAMPLES

Example 1

Bead Displacement.

The ability of ultrasound to displace micron scale beads was tested with several types of beads, several cell configurations and several ultrasonic power configurations. The position of the beads was determined with an optical microscope.

Experimental Details:

i. Ultrasound: Model 250 sonic disrupter, Bransonic ultrasonics. This is a 250 W, 20 kH ultrasonic source with microtip horn. The commercial power supply can produce up to 200 microns of tip displacement but we by-passed this source and used a 0–10 V peak-to-peak signal with a function generator. This level of power is much less than is supplied with the lowest level of the commercial power supply.

ii. Beads: Dynal M-280 and M-450 beads and Seradyne beads were studied. The Dynal beads were either 2.8 or 4.5 microns in diameter, have a density of ~1.34 gm/cm3 and are functionalized with tosyl groups. The Seradyne beads are 0.8–1.0 microns in diameter, have a density of 1.5 gm/cm3 and are functionalized with carboxyl groups. As the volume (and weight) of the beads scales with the cube of their diameter, the force transduced to each type of bead is expected to differ significantly.

iii. Microscope: Both reflection (Zeiss Axiotech) and transmission (Axiovert) optical microscopes were used to monitor the position of the beads. Both microscopes were connected to video cameras equipped with a digital frame grabber and image processing software. This software made it possible to determine the number and position of the beads.

iv. Cells: Several cells were used to determine the effect of cell dimensions and material properties. The two prefabricated cells tested were a polystyrene microtiter cell and glass microscope slide. Cells were also constructed from a ¼" aluminum plate with an ultrathin plastic bottom and a glass coverslip.

The beads were added to the wells in PBS buffer and allowed to sit for approximately one hour. From previous experience, we know that under these conditions the beads adhere to the surface so strongly that they can not be removed using the magnetic force generated by strong permanent magnets. All the beads were violently displaced from the surface in both the microtiter well and microscope slide cells when the microtip of the ultrasound was placed in direct contact with the solution (as in FIG. 2).

The beads could not be displaced from either cell when microtip was placed beneath the well in a transmission mode (FIG. 1). The difference in behavior is attributed to the severe attenuation of the ultrasound when it is transmitted through the thick walls of the microtiter well or microscope slide. To overcome this limitation, a cell was constructed from a ¼" diameter well machined in an aluminum plate with a 70 micron thick plastic bottom. When the tip of the ultrasound was placed in direct contact with the plastic bottom the beads were displaced at voltages between 5–10 Vpp. It is important to note that the initiation of the displacement of the beads took place at a critical voltage, thereby demonstrating force differentiation. This voltage differed from well to well and across a field of view in any given well. We attribute the well to well variation in force transduction to differences in mechanical transduction efficiency resulting from variations in loading and positioning.

The first beads that were displaced in a well were those directly under the ultrasonic source. However, beads were displaced at different levels of sound across the plastic membrane. In some places the beads were completely displaced while in others no beads were displaced. This behavior suggests that ultrasound excited standing waves in the plastic bottom. In fact, beads that were displaced were observed to travel across the surface of the cell and concentrate a specific points. This mode of force transduction produces complex force trajectories across the well but can be used to determine the intermolecular force if it can be referenced to other specific intermolecular interactions.

Beads were also displaced in the transmission mode using a coverslip cell.

Example 2

Demonstration of Force Differentiation.

The capacity of ultrasound to identify specific molecular interactions was demonstrated using streptavidin-biotin. This interaction is among the strongest occurring in nature.

The capacity of ultrasound to displace specifically bound beads was tested with Seradyne beads functionalized with streptavidin and biotin through a monolayer of polymeric polyethylene glycol (See, for example, U.S. pat. application Ser. No. 09/008,782, filed Jan. 20, 1998 by the same inventor and having the same assignee. This application is incorporated herein by reference). The cell was also functionalized with biotin using a PEG coating. The polymeric coating was used to minimize nonspecific forces.

Ultrasound was delivered through the bottom of the aluminium/plastic wells and the position of the beads was monitored with the Axiotech microscope. The ultrasound almost totally displaced the biotin beads, which migrated to a node on the surface. The streptavidin beads were not displaced by the ultrasound up to a 10 Vpp power level. This power level was always observed to displaced unfunctionalized beads.

Obviously, many modifications and variations of the present invention are possible in light of the above teachings. It is therefore to be understood that, within the scope of the appended claims, the invention may be practiced otherwise than as specifically described.

What is claimed is:

1. A device for characterizing the binding forces between a first binding member and a second binding member, the device comprising one or more particles that have a second binding member attached thereto, a reaction vessel that includes an inner surface that has a first binding member attached thereto and means for exposing the surface to the particles whereby, if the first binding member has a binding affinity for the second binding member, a complex is formed between individual first binding members and individual second binding members and the particles thereby become immobilized with respect to the surface, ultrasonic force means operatively disposed with respect to the surface for applying a variable force on the particles, and means for monitoring the position of the particles with respect to the surface.

2. The device of claim 1 wherein the variable force on the particles can be varied between an amount of force that is insufficient to separate the complex between the first binding member and the second binding member and an amount of force that is sufficient to separate the complex.

3. The device of claim 1 wherein the ultrasonic force means is an ultrasonic transducer capable of applying a pulsed ultrasonic force, and wherein the amplitude, frequency, pulse duration and/or wave-form of the ultrasonic force are selectable.

4. The device of claim 3 wherein the frequency of the pulsed ultrasonic force is between about 80 kHz and about 10 MHz.

5. The device of claim 1 wherein the pulse duration of the pulsed ultrasonic force is less than about 20 milliseconds.

6. The device of claim 1 wherein the wave-form of the pulsed ultrasonic force is a triangle or saw-tooth.

7. The device of claim 1, wherein said means for monitoring the position of the particles with respect to the surface comprises an optical microscope.

8. The device of claim 7, wherein said position-monitoring means further comprises a digital image acquisition system.

9. The assay device of claim 8, wherein said position monitoring means further comprises a digital image processing system, for identifying images of particles.

10. The device of claim 1, further comprising a counting means for counting particles.

11. The device of claim 1, wherein said particles have an average diameter between about 5 nm and about 1 mm.

12. The device of claim 1 wherein the particles are magnetic and wherein the device further includes means for applying a magnetic force to the particles.

13. The device of claim 1 wherein the device further includes means for applying additional force to the particles, said additional force being selected from the group consisting of magnetic force, optical force, hydrodynamic force, electrostatic force, gravitational force and combinations thereof.

14. A device for characterizing the binding forces between a plurality of different surface-bound binding members and a particle-bound binding member, the device comprising a surface that has spatially distinguishable subregions, wherein each subregion has a different surface-bound binding member attached thereto, a plurality of particles that have a particle-bound binding member attached thereto, a reaction vessel that includes means for exposing the subregions of the surface to the particles whereby, if a surface-bound binding member has a binding affinity for a particle-bound binding member, a complex is formed between individual surface-bound binding members and individual particle-bound binding members and the particles thereby become immobilized with respect to the surface, ultrasonic force means operatively disposed with respect to the surface for applying a variable force on the particles, and means for monitoring the position of the particles with respect to the subregions of the surface.

15. A device for characterizing the binding forces between a surface-bound binding member and a plurality of different particle-bound binding members, the device comprising a surface that has a surface-bound binding member attached thereto, a plurality of particles of different distinguishable classifications wherein each different distinguishable classification of particles has a different particle-bound binding member attached thereto, a reaction vessel that includes means for exposing the surface to the particles whereby, if a surface-bound binding member has a binding affinity for a particle-bound binding member, a complex is formed between individual surface-bound binding members and individual particle-bound binding members and the particles thereby become immobilized with respect to the surface, ultrasonic force means operatively disposed with respect to the surface for applying a variable force on the particles, and means for distinguishing between particles of different classifications and for monitoring the position of particles of each classification with respect to the surface.

16. A device for characterizing the binding force between a first binding member and a second binding member, the device comprising at least one assay cell that includes a cell wall having an outside surface and an inner surface, wherein the inner surface has been chemically modified by the attachment of a first binding member a test medium including one or more particles that have been chemically modified by the attachment of a second binding member, a reaction vessel that includes means for exposing the surface to the test medium whereby, if the first binding member has a binding affinity for the second binding member a complex is formed and the particles thereby becomes immobilized with respect to the surface, ultrasonic force means in contact with the outer surface of the assay cell and operatively disposed with respect to the surface for applying a variable ultrasonic force through the cell wall and onto the inner surface, and means for monitoring the position of the particles with respect to the surface.

17. A method for characterizing the binding forces between a first binding member and a second binding member, the method comprising the steps of (a) providing
(i) a surface that has a first binding member attached thereto and
(ii) a plurality of particles that have a second binding member attached thereto, (b) contacting the particles with the surface under conditions such that if the first binding member has a binding affinity for the second binding member, a complex is formed and the particle that the second binding member is attached to thereby becomes immobilized with respect to the surface, (c) applying a force from an ultrasonic power source to the particles, and (d) monitoring the position of the particles with respect to the surface before, during and/or after step (c).

* * * * *